(12) United States Patent
Schubert et al.

(10) Patent No.: US 7,754,647 B2
(45) Date of Patent: Jul. 13, 2010

(54) ACTIVATED METATHESIS CATALYSTS

(75) Inventors: Markus Schubert, Ludwigshafen (DE); Michael Hesse, Worms (DE); Juergen Stephan, Mannheim (DE); Volker Boehm, Frankenthal (DE); Andreas Brodhagen, Dannstadt-Schauernheim (DE); Frank Poplow, Ludwigshafen (DE); Martina Sinner-Lang, Ludwigshafen (DE); Uwe Diehlmann, Hassloch (DE); Gerhard Cox, Bad Duerkheim (DE); Jochen Pfeifer, Ilbesheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/098,165

(22) Filed: Apr. 4, 2008

(65) Prior Publication Data

US 2008/0254976 A1 Oct. 16, 2008

Related U.S. Application Data

(62) Division of application No. 10/819,978, filed on Apr. 8, 2004, now abandoned.

(30) Foreign Application Priority Data

Apr. 30, 2003 (DE) .............................. 103 19 439

(51) Int. Cl.
*B01J 23/00* (2006.01)
*B01J 21/08* (2006.01)
*B01J 20/00* (2006.01)
*B01J 29/00* (2006.01)

(52) U.S. Cl. .................. 502/254; 502/60; 502/104; 502/108; 502/109; 502/113; 502/255; 502/300; 502/305; 502/308; 502/309; 502/310; 502/349; 502/350; 502/351; 502/355; 502/415; 502/439

(58) Field of Classification Search ................ 502/60, 502/254, 300, 305, 308, 309, 310, 349, 350, 502/351, 352, 355, 415, 439, 104, 108, 109, 502/111, 113
See application file for complete search history.

(56) References Cited

U.S. PATENT DOCUMENTS 3,546,314 A 12/1970 Larson
3,586,731 A 6/1971 Heckelsberg (Continued)

FOREIGN PATENT DOCUMENTS

FR 1 370 025 8/1964

OTHER PUBLICATIONS

J. C. Mol, "Alkene Metathesis", Handbook of Heterogeneous Catalysis, vol. 5, Chapter 4.12.2.1, pp. 2387-2400.

(Continued)

*Primary Examiner*—Cam N Nguyen
(74) *Attorney, Agent, or Firm*—Oblon, Spivak, McClelland, Maier & Neustadt, L.L.P.

(57) ABSTRACT

The present invention provides a process for preparing a supported catalyst (catalyst C) having a support (support S) selected from among oxides, phosphates, silicates, carbides, borides and nitrides of main group elements and elements of transition groups VI and II and mixtures of the abovementioned compounds and an active component (activator A) comprising one or more compounds containing one or more elements of transition groups V, VI and VII customary for the catalysis of metathesis reactions.

9 Claims, 1 Drawing Sheet

U.S. PATENT DOCUMENTS

| | | | |
|---|---|---|---|
| 3,799,887 A * | 3/1974 | Brennan | 502/331 |
| 3,952,070 A | 4/1976 | Nowak et al. | |
| 4,024,201 A | 5/1977 | Takahashi | |
| 4,709,115 A | 11/1987 | Jung et al. | |
| 4,737,482 A * | 4/1988 | Yeh et al. | 502/220 |
| 5,196,389 A | 3/1993 | Dubots | |
| 5,399,324 A * | 3/1995 | Subramanian et al. | 423/213.7 |
| 6,043,395 A * | 3/2000 | Langer et al. | 564/450 |
| 6,177,375 B1 * | 1/2001 | Pullukat et al. | 502/104 |
| 6,184,430 B1 | 2/2001 | Venkatesh et al. | |
| 6,291,611 B1 * | 9/2001 | Kallio et al. | 526/129 |
| 6,506,858 B1 * | 1/2003 | Knuuttila et al. | 526/161 |
| 6,605,560 B1 * | 8/2003 | Chang | 502/104 |
| 2001/0045063 A1 | 11/2001 | Kambe et al. | |
| 2005/0065022 A1 | 3/2005 | Ying et al. | |

OTHER PUBLICATIONS

Klaus Weissermel, et al., "Olefin Metathesis", Industrial Organic Chemistry, Fourth Edition, Chapter 3.4, pp. 85-89.

* cited by examiner

ACTIVATED METATHESIS CATALYSTS

CROSS-REFERENCE TO RELATED APPLICATIONS

The present application is a divisional of U.S. Ser. No. 10/819,978, filed on Apr. 8, 2004 (now abandoned), which claims priority to DE 10319439.8, filed on Apr. 30, 2003.

BACKGROUND OF THE INVENTION

Field of the Invention

The present invention relates to a process for preparing a supported catalyst (catalyst C) comprising a support (support S) and an active component (activator A), wherein
a) a catalyst precursor is prepared by applying an activator customary for the catalysis of metathesis reactions (activator precursor) to a customary support (step a),
b) the catalyst precursor prepared in step a) is brought into contact with a hydrocarbon compound at from −20 to 550° C. (step b) and
c) the catalyst precursor prepared in step b) is heated at from 410 to 850° C. in an inert gas atmosphere (step c).

Furthermore, the invention relates to catalysts (catalysts C) which are obtainable by this process and to a process for preparing unsaturated compounds by metathesis using a catalyst (C).

The metathesis of unsaturated compounds is a long-established method of breaking and rearranging C—C bonds (e.g. Mol, J. C., Chapt. 4.12.2 "Alkene Metathesis" in "Handbook of Heterogeneous Catalysis", Eds. Ertl, G., Knözinger, H., Weitkamp, J., VCH, Weinheim 1997; Weissermehl, K., Arpe, H.-J., Chapt. 3.4 "Olefin-Metathese" in "Industrielle Organische Chemie", 4th edition, VCH, Weinheim 1994).

Various types of catalysts have been described for heterogeneously catalyzed metathesis. For the temperature range up to 120° C., the use of supported $R_2O_7$ or $Re(CO)_{10}$ catalysts is customary (Mol, J. C., Chapt. 4.12.2 "Alkene Metathesis" in "Handbook of Heterogeneous Catalysis", Eds. Ertl, G., Knözinger, H., Weitkamp, J., VCH, Weinheim 1997). However, rhenium is a rare and relatively expensive element, so that the use of such a catalyst is often uneconomical. At somewhat higher temperatures up to 400° C., catalysts based on $MoO_3$, $CoO$—$MoO_3$, $MoS_2$, $Mo(CO)_6$ or various supported Mo complexes can be employed according to the literature, and at even higher temperatures up to 540° C., systems based on $WO_3$, $WS_2$, $W(CO)_6$ or supported W complexes can be employed (Mol, J. C., Chapt. 4.12.2 "Alkene Metathesis" in "Handbook of Heterogeneous Catalysis", Eds. Ertl, G., Knözinger, H., Weitkamp, J., VCH, Weinheim 1997; Weissermehl, K., Arpe, H.-J., Chapt. 3.4 "Olefin-Metathese" in "Industrielle Organische Chemie", 4th edition, VCH, Weinheim 1994; Heckelsberg, L. F., Banks, R. L., Bailey, G. C., Ind. Eng. Chem. Prod. Res. Develop. 8 (1969), 259-261). Although these are very inexpensive, they generally have a significantly lower activity and also display lower selectivities. The reduced selectivities are a consequence of double bond isomerization which proceeds in parallel to metathesis over the strongly acidic molybdenum and tungsten compounds at relatively high reaction temperatures, which leads to the formation of undesirable products.

To suppress the secondary reaction of double bond isomerization, U.S. Pat. No. 3,586,731 describes the addition of alkali metal salts or alkaline earth metal salts to silica-supported oxides, sulfides or hexacarbonyls of tungsten, molybdenum or rhenium. However, this can lead to a considerable decrease in the catalyst activity.

U.S. Pat. No. 4,024,201 proposes adding halogen-containing compounds or amines to the feed to a supported $WO_3$ catalyst. However, such polar compounds are at the same time known as catalyst poisons in metathesis, so that a greatly reduced activity may also be expected here.

SUMMARY OF THE INVENTION

It is an object of the present invention to prepare a catalyst having increased metathesis activity and selectivity.

We have found that this object is achieved by the process and catalysts defined at the outset.

DETAILED DESCRIPTION OF THE INVENTION

Figure 1:
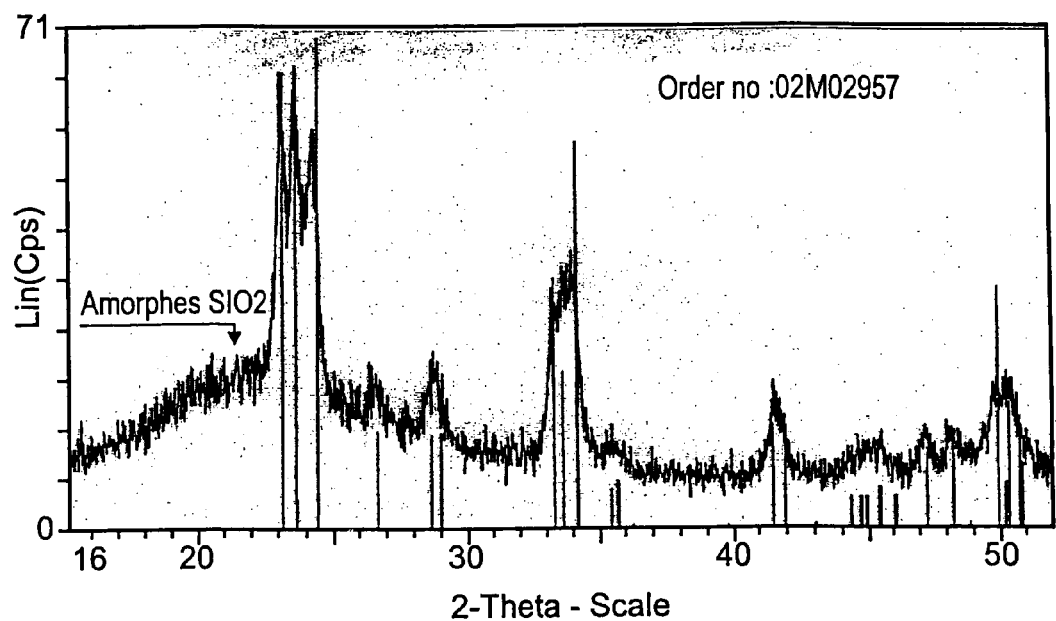
FIG. 1 shows the measurement on catalyst F/0 at room temperature as described in Example 5.

The catalyst precursors which are prepared in step a) and are subsequently reacted further in steps b) and c) to give the catalysts C of the present invention are the supported catalysts customarily used in metathesis reactions. Such catalysts are described, for example, in "Handbook of Heterogeneous Catalysis", edited by G. Ertl, H. Knözinger and J. Weitkamp, Volume 5, VCH Verlagsgesellschaft mbH, Weinheim, Chapter 4.12.2, Alkene Metathesis, pages 2387 to 2399.

Possible supports (support S) for the preparation of catalyst precursors are all materials customarily used for the preparation of supported catalysts, for example metal oxides, nitrides, borides, carbides, silicates, activated carbon, graphite. Preference is given to compounds of main group elements or elements of transition group VI or II and also mixtures of the abovementioned compounds. Particular preference is given to $Al_2O_3$, aluminosilicates, $Ga_2O_3$, $SiO_2$, $GeO_2$, $TiO_2$, $ZrO_2$, $SnO_2$ and mixtures of the abovementioned compounds. Suitable supports typically have a specific surface area of 10-500 $m^2/g$, preferably 100-400 $m^2/g$. The preferred pore volume (determined by means of mercury porosimetry) is from 0.3 to 1.3 ml/g. The preferred water absorption is from 0.5 to 1.5 ml/g. The supports are usually shaped bodies such as spheres, granules, extrudates or pellets. The support may have additionally been pretreated with acids.

The active components (activator precursors) applied to the support (S) in step a) include the customarily used compounds and mixtures thereof. These are generally compounds of the metals of transition groups V, VI and VII, in particular compounds of rhenium, tungsten or molybdenum. Possible compounds are the sulfides, oxides, nitrides, carbides, oxycarbides, carbonyls, organic complexes, halides, acids, polyacids, heteropolyacids and salts of the acids, polyacids and heteropolyacids. Such salts are preferably alkali metal or ammonium salts. In the present context, organic complexes are, for example, dialkyl complexes, acyl compounds, acetylacetonates or allyl complexes. Particular preference is given to molybdenum oxide and tungsten oxide. The term salts also includes substoichiometric bronzes. The term oxide extends not only to the stoichiometric compounds such as $MoO_3$, $WO_3$, $MoO_2$ and $WO_2$ but also includes substoichiometric phases of the type $MO_{3-x}$. As support for tungsten or molybdenum compounds, very particular preference is given to $SiO_2$.

In general, the preparation of the customary catalysts comprising oxides as activator precursors and serving as catalyst precursors is carried out in step a) by impregnating the support S with a solution of the abovementioned compounds. In the case of tungsten oxide, a solution of, for example, ammonium metatungstate, tungstic acid or tungsten pentachloride can be employed for this purpose. The impregnated supports are then usually dried in air at from 100 to 200° C. for a number of hours. This is usually followed by a calcination step. For this purpose, the impregnated and dried supports are usually heated in an oxygen-containing gas atmosphere, e.g. in air, at from 400 to 850° C. for a period of from about half an hour to 5 hours. The catalyst precursors prepared in this way can also be pretreated by means of heating steps in inert gas, for example $N_2$, $CO_2$ or noble gases, or be partially reduced in reducing gas mixtures comprising, for example, hydrogen, CO, ammonia or hydrazine.

To prepare the customary supported catalysts with carbides or oxycarbides as activator precursors which are included among the catalysts precursors, it is usual to start from the catalyst precursors comprising oxides as active component which have been prepared by the above method. In the carbiding step, the appropriate catalyst precursors comprising metal oxide are heated at from 550 to 800° C. in a hydrocarbon-containing stream, e.g. a methane stream, in the presence of hydrogen for, in general, a number of hours. The preparation of tungsten carbides typically requires temperatures about 50-200° C. higher than those for preparing molybdenum carbides. The properties of the carbides are also influenced by the $H_2/CH_4$ ratio which is typically 80/20. The appropriate carbiding methods are known and described, for example, in Oyama, S. T., Catal. Today, 15 (1992), 179.

After the carbiding step, these catalyst precursors have to be stored under an inert gas atmosphere because of their sensitivity to air, or they are passivated by means of dilute oxygen and then reactivated in the synthesis reactor. A further possibility is taking out the freshly prepared carbides under a liquid which substantially protects the carbide surface from atmospheric oxygen.

Furthermore, the following processes are also suitable for preparing catalyst precursors comprising carbides as activator precursors:

In J. Catal. 128, 126 (1991), Lee et al. describe the preparation of $Al_2O_3$-supported molybdenum carbides by (i) reduction followed by carbiding, (ii) direct carbiding in $CH_4/H_2$ or (iii) nitriding by means of $NH_3$ followed by carbiding.

Volpe, Boudart, J. Solid State Chem. 59, 332 (1985) and Volpe, Boudart, J. Solid State Chem. 59, 348 (1985) describe the nitriding/carbiding of $MoO_3$ and $WO_3$ in more detail.

The reduction of $MoO_3$ on carbon supports by means of hydrogen, which is coupled with carbiding by the carbon support above 530° C., is described, for instance, in Liang et al., Chem. Mater. 2002, 14, 3148.

Oxycarbides which can be used as activator precursors are described, for example, in Pham-Huu et al., Appl. Catal. A 132 (1995), 77. They can be prepared from the oxides by only partial carbiding. The oxycarbides are also formed under suitable conditions during the reaction when the oxide is used as starting material and a hydrocarbon/$H_2$ mixture is then passed over the catalyst at elevated temperatures (for instance: $H_2$/n-hexane=150, T=350° C.

The oxycarbides can also be prepared by treatment of carbides with oxygen. In Ledoux et al., New Frontiers in Catalysis, 1993, p. 955, Guczi, L. et al. (editors), Elsevier Science Publishers B.V., the carbide is firstly treated with air at 350° C. and then with hydrogen at the same temperature.

In step b), the catalyst precursors which have been prepared in this way are brought into contact with a hydrocarbon compound. Suitable hydrocarbon compounds are, in particular, aromatics, alkanes, cycloalkanes, alkynes, cycloalkynes, olefins or cycloolefins having from 1 to 20 carbon atoms. Particular preference is given to $C_3$-$C_{12}$-olefins, very particularly preferably butenes and octenes, e.g. 1-butene and n-1-octene.

In the treatment of the catalyst precursor with the hydrocarbon compound, the latter can be either in liquid or gaseous form. The treatment time is not critical and is usually 1 min-24 h, preferably 5 min-4 h. The temperature during the treatment is generally from –20 to 550° C., but is not critical. The latter also applies to the pressure, which is generally from 0.5 to 40 bar.

The catalyst precursor which has been treated with the hydrocarbon is subsequently heated to from 410 to 850° C., preferably from 500 to 850° C., in an inert gas atmosphere in step c). Suitable inert gases are, in particular, nitrogen, $CO_2$ and the noble gases. The treatment in step c) is usually carried out for from 5 minutes to 100 hours, preferably from 30 minutes to 24 hours, with the pressure once again being noncritical and usually being from 0.5 to 40 bar.

The catalysts (C) of the present invention may further comprise promoters. These are generally cobalt, alkali metal or alkaline earth metal compounds. They are generally applied to the catalyst by adding appropriate salts, e.g. nitrates or hydroxides, to the impregnation solutions for preparing the catalyst precursors, or by doping the catalysts afterward with an appropriate impregnation solution and calcining the catalysts once again to immobilize the dopant.

The proportion of activator (A) in the catalyst (C) is usually from 0.1 to 30% by weight.

The catalyst (C) particularly preferably comprises $WO_3$ in tetragonal form as activator (A) and $SiO_2$ as support (S).

The catalysts of the present invention are particularly useful for the metathesis of unsaturated compounds such as alkenes or alkynes. Such processes are generally known and are described, for example, in "Industrielle Organische Chemie", Klaus Weissermel, Hans-Jürgen Erpel, 5th edition, Wiley, VCH, 1998, Chapter 3.4 and "Handbook of Heterogeneous Catalysis", edited by G. Ertl, H. Knözinger and J. Weitkamp, Volume 5, VCH Verlagsgesellschaft mbH, Weinheim, Chapter 4.12.2, Alkene Metathesis, pages 2387 to 2399. However, they can also be used for the metathesis of unsaturated esters, nitriles, ketones, aldehydes, acids or ethers, as described, for example, in Xiaoding, X., Imhoff, P., von den Aardweg, C. N., and Mol, J. C., J. Chem. Soc., Chem. Comm. (1985), p. 273. In the reaction of substituted olefins, use is frequently made of a cocatalyst, for example tin, lead or aluminum alkyls, to increase the activity further.

The catalysts (C) of the present invention can be used in the same way as the known metathesis catalysts which are prepared as described in step a) of the process of the present invention and serve as catalyst precursors for the catalysts C of the present invention.

The catalysts of the present invention can be particularly advantageously used in metathesis processes for preparing propene by metathesis of a mixture comprising 2-butene and ethylene or 1-butene and 2-butenes, or for preparing 3-hexene and ethylene by metathesis of 1-butene. Appropriate processes are described in detail in DE-A-19813720, EP-A-1134271, WO 02/083609, DE-A-10143160.

The abovementioned $C_4$ starting compounds are usually supplied in the form of a raffinate II. The raffinate II is a $C_4$ fraction which generally has a butene content of from 30 to 100% by weight, preferably from 40 to 98% by weight. Apart from butenes, saturated $C_4$-alkanes in particular can also be present. The way in which such raffinates II are obtained is generally known and is described, for example, in EP-A-1134271.

In particular, it is possible to use 1-butene which is obtained by distilling off a 1-butene-rich fraction from raffinate II. 1-Butene can likewise be obtained from the remaining 2-butene-rich fraction by subjecting the 2-butene-rich fraction to an isomerization reaction and subsequently fractionally distilling the product to give a 1-butene-rich fraction and a 2-butene-rich fraction. This process is described in DE-A-10311139.

The rhenium-containing catalysts of the present invention are particularly useful for reactions in the liquid phase at from 10 to 150° C. and a pressure of from 5 to 100 bar.

The tungsten- or molybdenum-containing catalysts of the present invention are generally used in gas-phase reactions. The temperature here is generally from 150 to 500° C. The pressure is generally 5-50 bar.

EXAMPLES

Experimental Part

A. Preparation of the Catalysts

A.1. Preparation of the Catalyst Precursors

Example 1

Preparation of $WO_3/SiO_2$ Catalyst—Cats A-E $SiO_2$ supports were in each case impregnated with aqueous, dilute ammonium metatungstate solution to incipient wetness. The extrudates were then dried at 120° C. in a drying oven for 16 hours. The catalyst was finally treated under the conditions indicated in a rotary tube furnace and cooled under dry nitrogen (20 l/h). The catalyst C1 was then additionally impregnated with a 0.5 M NaOH solution and once again dried and calcined under the abovementioned conditions, as a result of which the Na content in the finished catalyst was increased from 1 100 to 4 500 ppm (=sample C2). Further details regarding the preparative conditions and the catalyst precursors themselves are given in table 1.

TABLE 1

| Cat | $WO_3$ content [wt %] | Support | Conditions in rotary tube furnace |
| --- | --- | --- | --- |
| A | 12.1 | BASF D11-10, 1.5 mm extrudates (171 m²/g) | 1 h in air (20 l/h), 593° C. |
| B | 13.9 | BASF D11-10, 1.5 mm extrudates (171 m²/g) | 1 h in air (20 l/h), 593° C. |
| C1 | 12.5 | BASF D11-10, 1.5 mm extrudates (171 m²/g) | 1 h in air (20 l/h), 593° C. |
| D | 11.2 | Shell X970 CY, 3 mm extrudates (326 m²/g) | 1 h in air (20 l/h), 593° C. |
| E1 | 15.0 | Solvay Siligel BR 5155/1, 0.8-2 mm spheres (350 m²/g) | 1 h in air (20 l/h), 593° C. |
| E2 | 15.0 | Solvay Siligel BR 5155/1, 0.8-2 mm spheres (350 m²/g) | 1 h in air (20 l/h), 593° C. + 2.5 h in $N_2$ (20 l/h), 850° C. |
| F | 12.2 | BASF D11-10, 0.5-0.8 mm granules (171 m²/g) | 1 h in air (20 l/h), 593° C. |

Example 2

Preparation of the Tungsten Carbide Catalyst—Cat G

To prepare catalyst G, 70 ml of the $WO_3/SiO_2$ catalyst A were placed in a glass reactor through which gas was passed from the top downward. The glass reactor was heated from the outside by means of an electric furnace, and the catalyst bed was located approximately in the middle of the heating zone on a glass frit. After the catalyst had been installed and the reactor had been closed, the plant was firstly flushed with nitrogen (30 min, 20 l/h). A gas stream comprising 3.9 l/h of methane and 15 l/h of hydrogen were subsequently passed over the catalyst. The reactor was then heated to 750° C. over a period of 180 minutes and held at 750° C. for 6 hours. It was then cooled to 500° C. over a period of 1 hour and this temperature was held for 2 hours. The reactor was then cooled and the methane/hydrogen stream was replaced by a stream of nitrogen. After the reactor had been flushed, the reactor inlet and outlet were closed and the reactor was removed from the plant in such a way that the catalyst could be transferred into a glove box without coming into contact with air. Contact with air was likewise avoided in subsequent handling of the catalyst, for instance the installation of the catalyst in the reactor or its introduction into analytical instruments.

An XRD (X-ray diffraction) pattern of the catalyst removed from the reactor after the metathesis reaction shows the compounds WC and $W_2C$ together with traces of metallic tungsten. $WO_x$ compounds are not observed.

Example 3

Preparation of an $MoO_3/SiO_2$ Catalyst—Cat H $SiO_2$ (BASF D11-10, 1.5 mm extrudates) was impregnated with an aqueous, dilute solution of $(NH_4)_6Mo_7O_{24}*4H_2O$ to incipient wetness. The extrudates were then dried at 120° C. in a drying oven for 16 hours. The catalyst was finally calcined at 593° C. in air (20 l/h) for 1 hour in a rotary tube furnace and cooled under dry nitrogen. The $MoO_3$ content was 11.1% by weight.

Example 4

Preparation of a $WO_3/SiO_2$ Catalyst—Cat J 508.2 g of $SiO_2$ (Shell X970 CY, 3 mm extrudates) were predried at 500° C. (air, 50 l/h). The cooled extrudates were impregnated with a solution of 70 g of $WCl_6$ in 1 200 ml of ethanol under a nitrogen atmosphere. The catalyst was subsequently dried in a stream of air (300 l/h, about 30 min) and calcined at 550° C. in air (50 l/h) for 2 hours. The catalyst was subsequently heated for another 2 hours at 850° C. under $N_2$ (50 l/h). The $WO_3$ content was 7.3%.

A.2 Activation of the Catalyst Precursors from Steps b) and c)

Example 5

Activation of the Catalysts (Methods 0-VII)

The catalysts were, with the exception of the comparative methods 0 and VII, each firstly brought into contact with a hydrocarbon, either directly in the reactor or by wetting with a liquid before installation of the catalyst. The catalysts which had been moistened with hydrocarbons were, with the exception of the comparative methods 0 and VI, subsequently heated under flowing nitrogen (30 l/h) to the temperature indicated for the time indicated and subsequently cooled to the reaction temperature under nitrogen. The conditions are reported in detail in table 2.

TABLE 2

| Method | Hydrocarbon | T (wetting) [° C.] | Time for which the hydrocarbon is allowed to act | T (heat treatment)[1]) [° C.] | Heat treatment time [h] |
|---|---|---|---|---|---|
| 0 (comp.) | Not applicable | Not applicable | Not applicable | Not applicable | Not applicable |
| I (comp.) | 1-Butene | 190[1)] | 3 h | 300 | 18 |
| II (comp.) | 1-Butene | 190[1)] | 3 h | 400 | 17 |
| III | 1-Butene | 190[1)] | 3-5 h | 510 | 16-20 |
| IV | n-1-Octene | Room temp. | 10 min | 510 | 15 |
| V | n-Octane | Room temp. | 10 min | 510 | 15 |
| VI (comp.) | n-1-Octene | Room temp. | 10 min | Not applicable | Not applicable |
| VII (comp.) | Not applicable | Not applicable | Not applicable | 510 | 17 |

[1)]The temperature reported is that at the entrance to the bed. As a result of a nonuniform temperature distribution of the heating, the temperature increases through to the end of the bed where it is about 10-15% higher.

In-Situ XRD Measurement on Catalysts F/0 and F/IV

Measurement on Catalyst F/0

Catalyst F/0 is a catalyst of the prior art and was prepared as described under point A.1, example 1 (method 0 in table 2). The catalyst F/0 was pulverized. The sample was introduced into the XRD measurement chamber on a heated alumina plate (depth: 0.8 mm). The measuring instrument is a model D8 Advance (from Bruker/AXS) equipped with a heated camera HTK 1200 from Paar. The measurement was carried out using Cu-K$_\alpha$ radiation in θ/θ geometry with a primary- and secondary-side Göbel mirror in the range 2θ=15°-52° at 6s/step at selected temperatures.

At room temperature, the sample in each case comprised monoclinic $WO_3$ and amorphous $SiO_2$ (FIG. 1). The sample was heated in air. At 400, 500 and 600° C., no change was observed. Only at 850° C. did tetragonal $WO_3$ form. The sample was then cooled to 200° C., resulting in the $WO_3$ transforming back into the monoclinic phase.

Measurement on Catalyst F/IV

Figure 2:
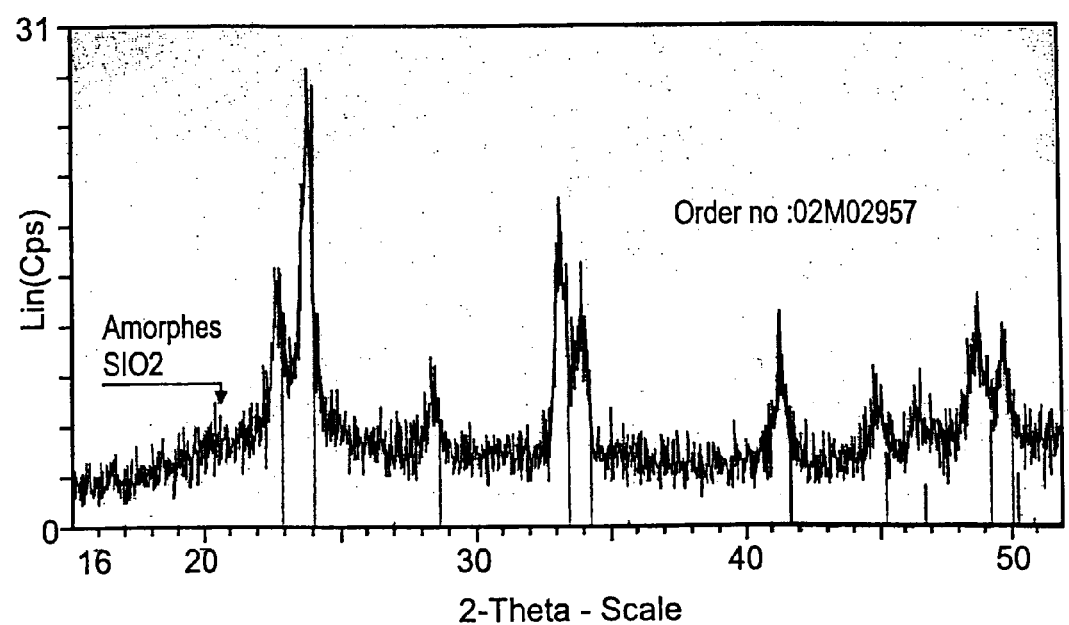
FIG. 2 shows the measurement on catalyst F/IV at 400° C. as described in Example 5.

The catalyst F/0 was pulverized and wetted with 1-octene. The sample was then introduced into the measuring apparatus described above and heated under a nitrogen atmosphere. Tetragonal $WO_3$ was formed at a temperature as low as 400° C. (FIG. 2). This phase remains stable at 500 and 600° C. In contrast to catalyst F/0, no transformation into the monoclinic phase occurred even after cooling to 200° C. It can be concluded from this that the catalyst F/0 has been changed irreversibly by the process of the present invention.

B. Metathesis Reactions

Examples 6-25

About 35 g of catalyst were placed in an electrically heated tube reactor. The temperature specified was set at the entrance to the catalyst bed. A nonuniform temperature distribution of the heating led to a rise in temperature through to the end of the catalyst bed (in each case reported in brackets). As feed pure 1-butene was fed in. The reaction pressure was 9.7 bar. Analysis of the output from the reactor was carried out on-line using a GC. Before the actual measurement, the catalysts had each been activated by the specified procedure 0-VI. The results are shown in table 3.

TABLE 3

| Ex. | Cat./meth. | T [° C.] | WHSV h$^{-1}$ | 1-Butene conversion [%] | Isomerization[1)] | Hexenes [mol %] | Propenes [mol %] | $C_6$ selectivity [mol %][2)] |
|---|---|---|---|---|---|---|---|---|
| 5 (comp.) | B/0 | 190 (256) | 7.9 | 66.6 | 66.4 | 0 | 0 | 0 |
| 6 (comp.) | C2/0 | 190 (249) | 7.9 | 24.7 | 24.5 | 0 | 0 | 0 |
| 7 (comp.) | D/0 | 190 (268) | 7.6 | 43.6 | 43.4 | 0 | 0.1 | 0 |
| 8 (comp.) | E1/0 | 190 (263) | 8.0 | 60.3 | 59.9 | 0.1 | 0.2 | 0.2 |
| 9 (comp.) | G/0 | 190 (303) | 8.7 | 52.6 | 51.5 | 0.2 | 0.8 | 0.8 |
| 10 (comp.) | H/0 | 190 (269) | 7.8 | 79.9 | 79.6 | 0.1 | 0.3 | 0.1 |
| 11 (comp.) | J/0 | 189 (242) | 15.1 | 14.0 | 13.0 | 0.3 | 0.2 | 7.9 |
| 12 (comp.) | A/VII | 189 (274) | 8.0 | 65.7 | 49.3 | 6.3 | 7.7 | 19.3 |
| 13 (comp.) | C1/VI | 190 (247) | 9.3 | 53.4 | 53.4 | 0 | 0 | 0 |
| 14 (comp.) | B/I | 190 (280) | 8.1 | 77.4 | 76.0 | 0.4 | 1.4 | 0.9 |
| 15 (comp.) | B/II | 190 (270) | 8.1 | 75.0 | 60.1 | 5.0 | 6.9 | 13.3 |
| 16 | B/III | 190 (256) | 8.1 | 62.4 | 43.1 | 7.8 | 9.6 | 24.9 |
| 17 | A/III | 189 (274) | 8.0 | 63.0 | 32.7 | 11.5 | 16.1 | 36.4 |
| 18a | C2/III | 189 (208) | 4.0 | 37.0 | 6.9 | 15.6 | 2.8 | 84.1 |

TABLE 3-continued

| Ex. | Cat./ meth. | T [° C.] | WHSV h$^{-1}$ | 1-Butene conversion [%] | Isomerization[1] | Hexenes [mol %] | Propenes [mol %] | C$_6$ selectivity [mol %][2] |
|---|---|---|---|---|---|---|---|---|
| 18b | C2/III | 190 (231) | 6.0 | 32.5 | 5.7 | 12.8 | 2.1 | 78.5 |
| 18c | C2/III | 190 (240) | 8.0 | 29.9 | 4.3 | 13.1 | 1.5 | 87.9 |
| 19 | D/III | 200 (244) | 7.6 | 47.8 | 11.5 | 16.8 | 7.8 | 70.3 |
| 20 | E1/III | 190 (251) | 7.4 | 46.5 | 13.5 | 14.6 | 7.3 | 62.8 |
| 21 (comp.) | E2/0 | 190 (228) | 7.7 | 43.5 | 23.0 | 8.7 | 7.4 | 40.0 |
| 22 | E2/III | 190 (228) | 7.2 | 47.0 | 12.8 | 16.6 | 6.5 | 70.5 |
| 23a | G/III | 155 (238) | 4.3 | 44.1 | 13.9 | 13.5 | 6.9 | 61.1 |
| 23b | G/III | 190 (293) | 8.8 | 52.8 | 22.5 | 13.4 | 10.2 | 50.8 |
| 24 | H/III | 190 (263) | 7.6 | 64.0 | 57.0 | 2.4 | 3.4 | 7.6 |
| 25a | J/III | 189 (212) | 4.0 | 41.2 | 8.2 | 17.9 | 4.3 | 86.0 |
| 25b | J/III | 190 (237) | 10.0 | 33.9 | 6.1 | 15.1 | 2.8 | 86.7 |
| 25c | J/III | 190 (240) | 14.9 | 38.7 | 4.8 | 16.7 | 2.6 | 86.3 |
| 25d | J/III | 170 (217) | 14.9 | 26.9 | 2.5 | 13.3 | 1.1 | 98.9 |
| 26 | E1/IV | 190 (247) | 7.7 | 43.2 | 14.8 | 12.2 | 6.9 | 56.7 |
| 27 | B/V | 190 (250) | 7.7 | 64.5 | 38.4 | 10.1 | 13.5 | 31.2 |

[1]Sum of the allyl fragments formed = [propene]/2 + 2-butene + pentenes
[2]C$_6$-Selectivity = 2 * C$_6$ yield/conversion (1-butene)

We claim:

1. A process for preparing a supported catalyst (catalyst C) comprising
    a support (support S) selected from the group consisting of an oxide, a phosphate, a silicate, a carbide, a boride and a nitride of a main group element and an element of transition groups VI and II, and mixtures thereof, and
    an active component (activator A) comprising one or more compounds containing one or more elements of transition groups V, VI and VII customary for the catalysis of metathesis reactions, wherein the process comprises
    a) preparing a catalyst precursor by applying an activator precursor of activator A to the support S,
    b) contacting the catalyst precursor prepared in step a) with a hydrocarbon compound at a temperature from −20 to 550° C., and
    c) heating the catalyst precursor prepared in step b) at a temperature from 410 to 850° C. in an inert gas atmosphere.

2. The process as claimed in claim 1, wherein the support (S) is selected from the group consisting of Al$_2$O$_3$, aluminosilicates, Ga$_2$O$_3$, SiO$_2$, GeO$_2$, TiO$_2$, ZrO$_2$, SnO$_2$ and mixtures thereof.

3. The process as claimed in claim 1, wherein the compounds of elements of transition groups V, VI and VII are selected from the group consisting of sulfides, oxides, nitrides, carbides, oxycarbides, carbonyls, organic complexes, halides, acids, polyacids, heteropolyacids and salts of the acids, polyacids and heteropolyacids.

4. The process as claimed in claim 1, wherein the activator precursor comprises compounds selected from the group consisting of rhenium, tungsten and molybdenum compounds.

5. The process as claimed in claim 4, wherein the activator precursor comprises compounds selected from the group consisting of molybdenum oxides, tungsten carbides and tungsten oxides.

6. The process as claimed in claim 1, wherein the activator precursor additionally comprises a promoter selected from the group consisting of cobalt, alkali metal and alkaline earth metal compounds.

7. The process as claimed in claim 1, wherein step a) is carried out by impregnating the support (S) with a solution of the activator precursor and subsequently drying it and optionally calcining it.

8. The process as claimed in claim 1, wherein the hydrocarbon compound used in step b) is selected from the group consisting of C$_1$-C$_{20}$-alkanes, -cycloalkanes, -olefins, -cycloolefins, -alkynes, -cycloalkynes, aromatics and mixtures thereof.

9. The process as claimed in claim 1, wherein the inert gas used in step c) is selected from the group consisting of nitrogen, carbon dioxide and noble gases and mixtures thereof.

* * * * *